(12) United States Patent
Eifert et al.

(10) Patent No.: US 11,721,441 B2
(45) Date of Patent: Aug. 8, 2023

(54) DETERMINING DRUG EFFECTIVENESS RANKING FOR A PATIENT USING MACHINE LEARNING

(71) Applicant: Merative US L.P., Ann Arbor, MI (US)

(72) Inventors: Cheryl L. Eifert, Watertown, MA (US); Jia Xu, Somerville, MA (US); Claudia S Huettner, Jamaica Plain, MA (US); Fang Wang, Plano, TX (US); Vanessa Michelini, Boca Raton, FL (US); Elinor Dehan, Haniel (IL)

(73) Assignee: MERATIVE US L.P., Ann Arbor, MI (US)

(*) Notice: Subject to any disclaimer, the term of this patent is extended or adjusted under 35 U.S.C. 154(b) by 1151 days.

(21) Appl. No.: 16/248,084

(22) Filed: Jan. 15, 2019

(65) Prior Publication Data
US 2020/0227176 A1 Jul. 16, 2020

(51) Int. Cl.
| | | |
|---|---|---|
| *G16H 70/40* | (2018.01) | |
| *G16B 50/00* | (2019.01) | |
| *G16B 40/00* | (2019.01) | |
| *G16H 70/60* | (2018.01) | |

(52) U.S. Cl.
CPC ............. *G16H 70/40* (2018.01); *G16B 40/00* (2019.02); *G16B 50/00* (2019.02); *G16H 70/60* (2018.01)

(58) Field of Classification Search
CPC ........ G16H 70/40; G16H 70/60; G16B 40/00; G16B 50/00
See application file for complete search history.

(56) References Cited

U.S. PATENT DOCUMENTS

| | | |
|---|---|---|
| 7,130,848 B2 | 10/2006 | Oosta |
| 7,461,006 B2 | 12/2008 | Gogolak |
| 8,903,825 B2 | 12/2014 | Parker et al. |
| 9,483,532 B1 | 11/2016 | Zhang et al. |
| 9,495,349 B2 | 11/2016 | Angell et al. |
| 9,690,861 B2 | 6/2017 | Boloor et al. |
| 10,093,982 B2 | 10/2018 | Sowadski et al. |
| 10,713,440 B2 | 7/2020 | Pestian et al. |
| 2001/0034023 A1 | 10/2001 | Stanton et al. |
| 2003/0177112 A1 | 9/2003 | Gardner |
| 2004/0142325 A1 | 7/2004 | Mintz et al. |
| 2005/0060305 A1 | 3/2005 | Hopkins et al. |
| 2007/0112748 A1 | 5/2007 | Angell et al. |
| 2008/0027913 A1 | 1/2008 | Chang et al. |
| 2009/0012956 A1 | 1/2009 | Wen et al. |
| 2009/0019032 A1 | 1/2009 | Bundschus et al. |
| 2011/0119212 A1 | 5/2011 | De Bruin et al. |
| 2011/0230360 A1* | 9/2011 | Stephan ............... C12Q 1/6886 435/7.1 |
| 2012/0116795 A1 | 5/2012 | Ledley |
| 2013/0013603 A1 | 1/2013 | Parker et al. |
| 2013/0091126 A1 | 4/2013 | Krishnaswami et al. |
| 2013/0096946 A1 | 4/2013 | Shah et al. |
| 2013/0144887 A1 | 6/2013 | Chen et al. |
| 2014/0278130 A1 | 9/2014 | Bowles et al. |
| 2014/0280086 A1 | 9/2014 | Bouadjenek et al. |
| 2015/0088888 A1 | 3/2015 | Brennan et al. |
| 2016/0019299 A1 | 1/2016 | Boloor et al. |
| 2016/0048564 A1 | 2/2016 | Bassett, Jr. et al. |
| 2016/0210426 A1 | 7/2016 | Robinson et al. |
| 2016/0232309 A1 | 8/2016 | Yoon et al. |
| 2016/0232321 A1 | 8/2016 | Silverman |
| 2017/0255743 A1 | 9/2017 | Torkamani |
| 2018/0060483 A1 | 3/2018 | Song et al. |
| 2018/0081859 A1 | 3/2018 | Snider et al. |
| 2018/0137249 A1 | 5/2018 | Eggebraaten et al. |
| 2018/0137433 A1 | 5/2018 | Devarakonda et al. |
| 2018/0211174 A1 | 7/2018 | Allen et al. |
| 2018/0373844 A1 | 12/2018 | Ferrandez-Escamez et al. |
| 2019/0034593 A1 | 1/2019 | Bouman |

(Continued)

FOREIGN PATENT DOCUMENTS

| | | |
|---|---|---|
| CN | 105138862 A | 12/2015 |
| CN | 108417271 A | 8/2018 |

(Continued)

OTHER PUBLICATIONS

List of IBM Patents or Patent Applications Treated as Related dated Mar. 25, 2019.
Tamborero et al., "Cancer Genome Interpreter Annotates the Biological and Clinical Relevance of Tumor Alterations" Genome Medicine (Mar. 28, 2018) 10(25): 8 pages, doi: https://doi.org/10.1101/140475.
International Search Report and Written Opinion in corresponding International Application No. PCT/IB2019/060507, dated Mar. 25, 2020, 9 pages.
Wei et al., "TmVar 2.0 integrating genomic variant information from literature with dbSNP and ClinVar for precision medicine." doi: 10.1093/bioinformatics/btx541. Bioinformatics. Jan. 1, 2018 ;34(1): pp. 80-87.
Allot et al., "LitVar: A Semantic Search Engine for Linking Genomic Variant Data in PubMed and PMC." Nucleic Acids Research, vol. 46. Web Server issue (2018): W530-W536. PMC. Web., Aug. 15, 2018, 7 pages.

(Continued)

*Primary Examiner* — Jerry Lin
(74) *Attorney, Agent, or Firm* — Edell, Shapiro & Finnan, LLC

(57) ABSTRACT

Computer based methods, systems, and computer readable media for intelligently accessing various types of pharmaceutical information in a content repository and ranking drugs at the variant level, gene level, and pathway level. In some cases, drugs that target the same gene, gene variant, or biological pathway may be ranked based upon in vitro, pre-clinical, clinical, or post-clinical evidence. To determine ranking of a plurality of drugs, information pertaining to drug administration is analyzed for the drugs. For a plurality of drugs, attributes corresponding to the drug are determined, wherein the attributes include a variant or a gene targeted by the drug, and a biological pathway comprising the targeted variant or gene. The plurality of drugs are ranked according to a drug effectiveness score based on one or more of a determined efficacy, potency, or toxicity.

20 Claims, 7 Drawing Sheets

(56) References Cited

U.S. PATENT DOCUMENTS

| | | |
|---|---|---|
| 2019/0042563 A1 | 2/2019 | Pestian et al. |
| 2019/0130073 A1 | 5/2019 | Sun et al. |
| 2020/0175020 A1 | 6/2020 | Eifert et al. |
| 2020/0175021 A1 | 6/2020 | Eifert et al. |
| 2020/0184006 A1 | 6/2020 | Eifert et al. |
| 2020/0218719 A1 | 7/2020 | Eifert et al. |
| 2020/0226164 A1 | 7/2020 | Eifert et al. |

FOREIGN PATENT DOCUMENTS

| | | |
|---|---|---|
| WO | 2016016879 A1 | 2/2016 |
| WO | 2018209161 A1 | 11/2018 |
| WO | 2019243486 A1 | 12/2019 |

OTHER PUBLICATIONS

Wei et al., "GNormPlus: An Integrative Approach for Tagging Genes, Gene Families, and Protein Domains." BioMed Res Int 2015, vol. 2015, Article ID 918710, http://dx.doi.org/10.1155/2015/918710, Sep. 2015, 7 pages.

Seva et al., "Track 4: Mining protein interactions and mutations for precision medicine (PM)," BioCreative, 2017 www.biocreative.org/media/store/files/2018/BC6_track4_13.pdf, 5 pages.

Yepes et al., "Mutation extraction tools can be combined for robust recognition of genetic variants in the literature" [version 2; referees: 2 approved, 1 approved with reservations], F1000Research 2014, 3:18 (doi: 10.12688/f1000research.3-18.v2), Nov. 2017, pp. 1-27.

Ravikumar et al., "Text Mining Facilitates Database Curation—Extraction of Mutation-Disease Associations from Bio-Medical Literature." BMC Bioinformatics, 16 (2015): 185, pp. 1-15.

Asma et al., "DiMeX: A Text Mining System for Mutation-Disease Association Extraction." PLoS ONE, 11(4): e0152725, 2016, 26 pages.

LexisNexus, "Developing a Search with LexistNexis." © 2014 LexisNexis. NBI01326-0 0414, https://www.lexisnexis.com/bis-user-information/docs/developingasearch.pdf, pp. 1-17.

U.S. National Library of Medicine, "Search Strategy Used to Create the Systematic Reviews Subset on PubMed," 2018, https://www.nlm.nih.gov/bsd/pubmed_subsets/sysreviews_strategy.html, Accessed Aug. 17, 2018, 2 pages.

U.S. National Library of Medicine, "PubMed Help," Bookshelf ID: NBK3827, 2018, https://www.ncbi.nlm.nih.gov/books/NBK3827, National Center for Biotechnology Information, Accessed Aug. 17, 2018, 125 pages.

Weng et al., "Medical Subdomain Classification of Clinical Notes Using a Machine Learning-Based Natural Language Processing Approach." BMC Medical Informatics and Decision Making 17 (2017): 155. PMC. Web., Aug. 16, 2018, pp. 1-13.

Kafkas et al., "Section Level Search Functionality in Europe PMC." Journal of Biomedical Semantics 6 (2015): 7. PMC. Web. Aug. 16, 2018, pp. 1-5.

Hofmann et al., "The impact of document structure on keyphrase extraction." In Proceedings of the 18th ACM conference on Information and knowledge management (CIKM '09). ACM, New York, NY, USA, 2009, pp. 1725-1728.

Xu et al., "A semi-supervised approach to extract pharmacogenomics-specific drug-gene pairs from biomedical literature for personalized medicine," Journal of Biomedical Informatics, vol. 46, Issue 4, 2013, pp. 585-593.

Lee et al., "Deep learning of mutation-gene-drug relations from the literature." BMC Bioinformatics (2018), 19:21. Published: Jan. 25, 2018, pp. 1-13.

Huang et al., "Predicting drug efficacy based on the integrated breast cancer pathway model," 2011 IEEE International Workshop on Genomic Signal Processing and Statistics (GENSIPS), San Antonio, TX, Dec. 2011, pp. 42-45.

Artemov et al., "A Method for Predicting Target Drug Efficiency in Cancer Based on the Analysis of Signaling Pathway Activation." Oncotarget, vol. 6, No. 30, www.impactjournals.com/oncotarget/, Aug. 2015, pp. 29347-29356.

Allahyari et al., "A Brief Survey of Text Mining: Classification, Clustering and Extraction Techniques", https://arxiv.org/pdf/1707.02919.pdf, Cornell Library University, arXiv:1707.02919v2 [cs.CL], Jul. 28, 2017, 13 pages.

Clematide et al., "Ranking Relations between Diseases, Drugs and Genes for a Curation Task", Journal of Biomedical Semantics, https://jbiomedsem.biomedcentral.com/articles/10.1186/2041-1480-3-S3-S5, Oct. 5, 2012, pp. 1-22.

Wu et al.; "Ranking Gene-Drug Relationships in Biomedical Literature using Latent Dirichlet Allocation", NCBI, https://vww.ncbi.nlm.nih.gov/pmc/articles/PMC4095990/; Pac Symp Biocomput, Author manuscript, Jul. 14, 2014, pp. 1-15.

Chen et al., "IBM Watson: How Cognitive Computing Can Be Applied to Big Data Challenges in Life Sciences Research". Clinical Therapeutics, 2016, 38(4):688-701. doi: 10.1016/j.clinthera.2015.12.001. Epub Apr. 21, 2016, pp. 688-701.

NCBI, "PubMed", US National Library of Medicine National Institute of Health, 2018; https://www.ncbi.nlm.nih.gov/pubmed/ (accessed Nov. 30, 2018), 2 pages.

U.S. National Library of Medicine, "MEDLINE/PubMed Resources Guide", 2018, https://www.nlm.nih.gov/bsd/omresources html (accessed Nov. 30, 2018), 7 pages.

Wei et al., "TmVar: a text mining approach for extracting sequence variants in biomedical literature", Original Paper, BIOINFORMATICS, vol. 29, No. 11, Apr. 5, 2013, https://academic.oup.com/bioinformatics/article/29/11/1433/220291, 7 pages.

\* cited by examiner

DRUG 1
FIRST BIOLOGICAL TARGET (GENE X, PROTEIN Z)
TOXICITY (UNKNOWN)
IC50-1
SECONDARY BIOLOGICAL TARGETS - LINKED TO TOXICITY BY ML

DRUG 2
FIRST BIOLOGICAL TARGET (GENE X, PROTEIN Z)
TOXICITY (TOXICITY Y2)
IC50-2
SECONDARY BIOLOGICAL TARGETS - NO KNOWN TOXICITY FROM ML
SIDE CHAIN A2

DRUG 3
FIRST BIOLOGICAL TARGET (GENE X, PROTEIN Z)
TOXICITY (UNKNOWN)
IC50-3
SIDE CHAIN A1 - LINKED TO TOXICITY BY ML

FIG. 5

DETERMINING DRUG EFFECTIVENESS RANKING FOR A PATIENT USING MACHINE LEARNING

1. TECHNICAL FIELD

Present invention embodiments relate to drug effectiveness, and more specifically, to using machine learning to analyze drug information to generate drug effectiveness rankings for a patient and to intelligently search and extract content related to drug administration.

2. DISCUSSION OF THE RELATED ART

Databases and article repositories often contain a large corpus of documents of varying types of information. For example, a user may search NCBI's PubMed® database for different types of peer-reviewed scientific and clinical documents. Numerous drugs may potentially be available to treat patients who have diseases driven by a common genomic alteration such as HER-2 positive breast cancers. However, the efficacy and potency of each of these individual drugs often varies significantly among patients.

While there are a variety of databases available which cover clinical and experimental information, these databases do not adequately cover specialized information pertaining to pharmaceutical drugs and biologics. Although some systems are geared towards anticancer treatments, covering approved and investigational drugs, these systems do not provide specific and specialized information regarding drug efficacy, potency, and other aspects related to drug administration.

Additionally, access to full-length research documents in PubMed® is often granted only if an institutional license agreement has been implemented with the journal's publisher or another form of payment has been submitted to acquire the rights to the full-length document. To ensure the accuracy of the data, users must be able to evaluate figures, graphs, tables and text within the results section of the documents. In some cases, content repositories may maintain millions of documents with no intelligent way to access complete content.

Content repositories do not provide user interfaces for specific content searching pertaining to efficacy and other features of pharmaceutical drugs and biologics. Accordingly, relevant information is often missed, and patients may not be matched with optimal drugs or combinations thereof.

SUMMARY

According to embodiments of the present invention, methods, systems and computer readable media are provided for intelligently accessing various types of pharmaceutical information in a content repository and ranking drugs at the gene variant level, gene level, and biological pathway level. In some cases, drugs that target the same gene/biological pathway may be ranked based upon pre-clinical, clinical, or post-clinical evidence including drug characteristics.

Extracted information pertaining to drug characteristics is analyzed for a plurality of drugs. For each drug, one or more drug characteristics including toxicity, potency, and/or efficacy are determined. The drug is associated with a plurality of attributes including a variant or a gene targeted by the drug, and a biological pathway comprising the targeted variant or gene. The plurality of drugs are ranked according to a drug effectiveness score based on the drug characteristics. This approach relies on clinical evidence to ascertain drug properties in order to provide an optimal or effective ranking of drugs for a specified target.

In some aspects, drug characteristics may include any parameter used to evaluate drug performance or effectiveness including efficacy, toxicity, and potency. Present techniques allow for drugs with high potency and efficacy and low toxicity to be identified and prioritized for administration to a patient. Drug characteristics are not limited to potency, efficacy and toxicity, as any suitable drug characteristic may be used to identify and rank drugs.

In another embodiment, the extracted information comprises pre-clinical, clinical, and post clinical information, from which drug characteristics are extracted. Thus, present techniques utilize evidence from the clinical literature. This information may be used to create a training data set for a machine learning module to predict drug characteristics of other drugs for which such characteristics may not be available in the literature.

In other aspects, a machine learning module may be trained with training data sets generated from the extracted information. For drugs not in the training data set, one or more drug characteristics for each drug of the plurality of drugs may be predicted by the trained machine learning module. The drugs may be ranked for treatment of a patient-specific cancer, wherein each drug targets a particular gene, gene variant, or biological pathway associated with the patient's cancer, and wherein the ranking is based on the predicted drug characteristics according to a drug effectiveness score. Accordingly, present techniques provide ranking information on drugs for a specific patient.

In other aspects, for a plurality of drugs, common structural features and corresponding drug characteristics may be identified, including toxicity. Using a machine learning module trained on information identifying the common structural features and the drug characteristics, other drugs may be predicted to be associated or not associated with toxicity. Likewise, drugs with a high risk of toxicity may be analyzed by a machine learning module to predict chemical structures associated with toxicity. Present techniques predict toxicity, and this result may be used to identify optimal drugs having a low risk of toxicity and other undesirable side effects.

In other aspects, the plurality of drugs may be classified into groups based on a common target, and the drugs may be ranked within each group. Thus, optimal drugs for a specific target (and for a specific patient) may be identified in an effective manner.

In other aspects, drug attributes comprise patient-specific information indicating a gene, a gene variant or a biological pathway for a patient, and further comprise identifying a plurality of drugs that target the gene, the gene variant or the biological pathway(s) of the patient. The identified drugs may be ranked according to a drug effectiveness score based on the drug characteristics. Thus, drugs may be ranked based on attributes and drug characteristics according to a drug effectiveness score in a patient-specific manner.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

FIG. 5 is an illustration showing an example of different drug profiles, according to embodiments of the present disclosure.

DETAILED DESCRIPTION

Personalized cancer medicine involves matching an oncogenic mutation from the patient to the appropriate targeted drug therapy. A drug (e.g., pharmaceutical, biologic, etc.) may include any suitable therapy in pre-clinical, clinical, or post-clinical studies. Methods, systems, and computer readable media are provided herein to rank drugs according to a drug effectiveness score based on drug characteristics for a specific patient.

Documents pertaining to pre-clinical, clinical, or approved drugs may be accessed and analyzed to determine relationships between drugs, genes, gene variants, and biological pathways for a specific disease such as a type of cancer. A user interface, which may be provided within a document management portal, enables the user to query a database regarding drug efficacy or other drug characteristics (e.g., drug potency, drug toxicity, etc.) for a particular type of cancer.

To achieve this, evidence related to drug administration (e.g., efficacy, potency, toxicity, secondary effects (such as off target effects), IC50, ED50, etc.) may be extracted from the clinical information. Once the relevant information is extracted, drugs and their corresponding characteristics may be analyzed by a machine learning system in terms of efficacy and other characteristics (e.g., toxicity, potency, etc.) at the gene level, gene variant level, or biological pathway level to determine optimal drugs for a specific oncogenic mutation. The drugs may be ranked for a specific patient for a specific type of disease, such as cancer.

Figure 1:
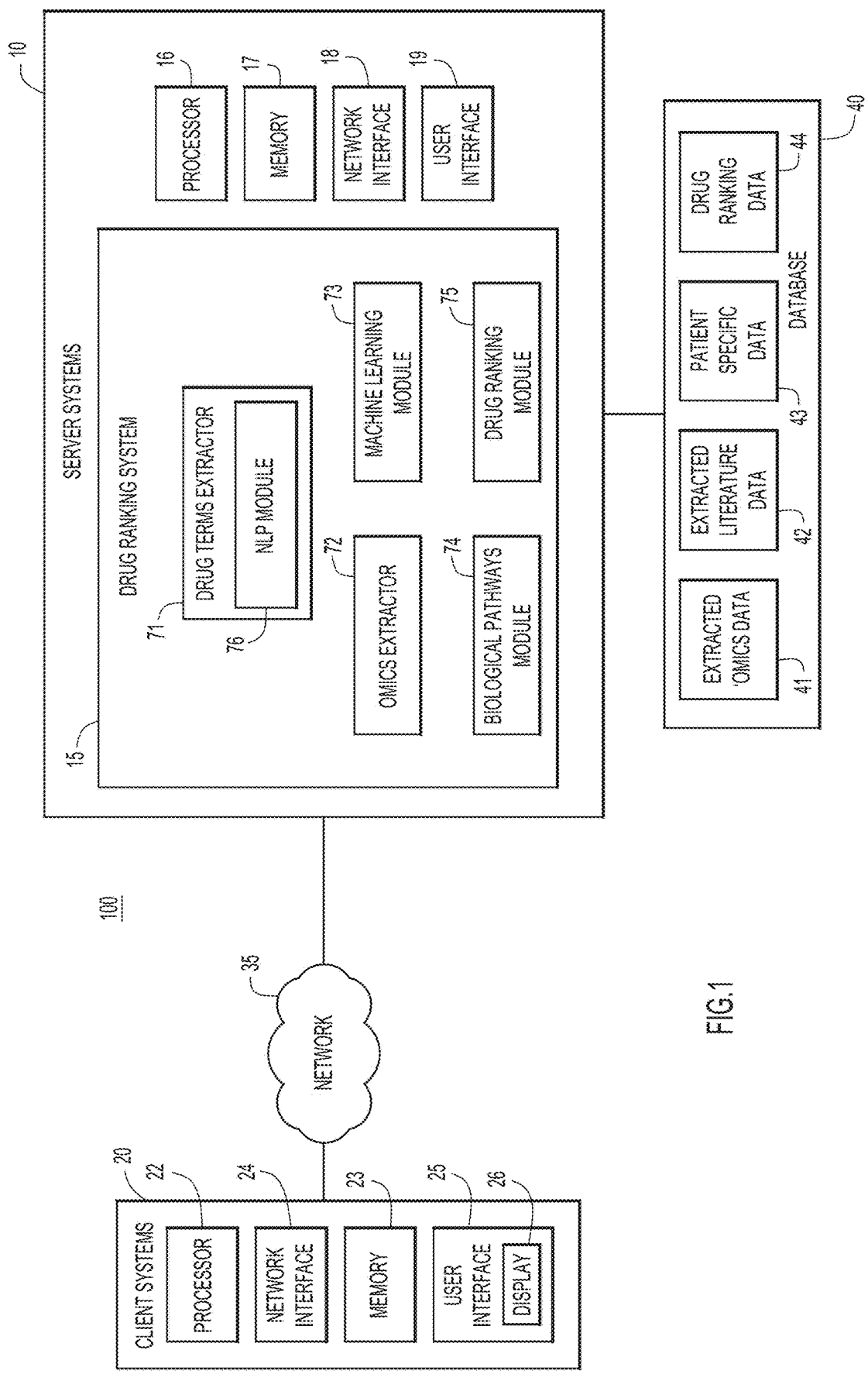
FIG. 1 is a block diagram of an example computing environment for the drug ranking system, according to embodiments of the present disclosure.

An example environment 100 for use with present invention embodiments is illustrated in FIG. 1. Specifically, the environment includes one or more server systems 10, and one or more client or end-user systems 20. Server systems 10 and client systems 20 may be remote from each other and communicate over a network 35. The network may be implemented by any number of any suitable communications media (e.g., wide area network (WAN), local area network (LAN), Internet, Intranet, etc.). Alternatively, server systems 10 and client systems 20 may be local to each other, and communicate via any appropriate local communication medium (e.g., local area network (LAN), hardwire, wireless link, Intranet, etc.).

Client systems 20 enable users to access documents and information (e.g., clinical documents, extracted literature data, extracted omics data, drug ranking information, patient-specific information, biological pathways, etc.) from server systems 10 for analysis and review. The server system may include a drug ranking system 15 to rank drugs in order to select and prioritize drugs for a specific patient.

A database system 40 may store various information for the analysis (e.g., extracted omics data 41, extracted literature data 42, patient specific data 43, drug ranking data 44, etc.). The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents and drug analysis, and may provide reports including analysis results (e.g., drug efficacy, ranking of drugs, toxicity of drugs, potency of drugs, ED50, IC50, biological targets of drugs (e.g., genes, gene variants, proteins, other cellular targets), biological pathways, secondary effects such as off target effects, etc.).

Server systems 10 and client systems 20 may be implemented by any conventional or other computer systems preferably equipped with a display or monitor 26, a base (e.g., including at least one processor 16, 22 one or more memories 17, 23 and/or internal or external network interfaces or communications devices 18, 24 (e.g., modem, network cards, etc.)), optional input devices (e.g., a keyboard, mouse or other input device) and/or user interface 19, 25 and any commercially available and custom software (e.g., server/communications software, drug ranking system 15, browser/interface software, etc.).

Alternatively, one or more client systems 20 may analyze documents to determine drug ranking when operating as a stand-alone unit. In a stand-alone mode of operation, the client system stores or has access to extracted omics data 41, extracted literature data 42, patient-specific data 43, and drug ranking data 44 as well as the drug ranking system 15. The graphical user (e.g., GUI, etc.) or other user interface (e.g., command line prompts, menu screens, etc.) may solicit information from a corresponding user pertaining to the drug ranking, and may provide reports including analysis results and drug ranking (e.g., ranking of drugs, drug efficacy, drug toxicity, drug potency, IC50, ED50, biological targets of drugs (genes, gene variants, proteins, other cellular targets), biological pathways, secondary effects such as off target effects, etc.).

Extracted omics data 41 and extracted literature data 42 may include extracted information from databases and/or literature that may indicate the presence of a disease in a patient. For example, extracted literature data may include genes and gene variants associated with diseases, along with corresponding expressed proteins, transcripts, or other relevant molecules, biological pathways, drug targets, toxicities, potencies, efficacies, secondary effects, IC50, ED50, etc. Literature documents are presumed to be readable by a machine reader. In some aspects, optical character recognition may be used to recognize text in a document, to render the text readable and searchable. Additionally, text in tables, images, image captions, or lists may also be rendered machine readable. This processing ensures that images of documents, e.g., scanned PDFs, are included in the analysis.

Literature data may include data from databases, scientific literature, and clinical and preclinical literature, as well as any other source of relevant information, which relates to biological targets of specific drugs that are in clinical trials or that have been approved by regulatory agencies. In some cases, this information includes a drug interaction with a specific biological molecule of a pathway (e.g., evidence that a drug binds to a biological molecule, inhibits a biological pathway, activates a biological pathway, off target effects including interaction with a secondary target, adverse effects, contraindications with other medicines, etc.). This allows biological targets to be associated with biological pathways, and a framework to be set up to study drug efficacy and specificity.

In some aspects, diseases may include a type of cancer such as breast, lung, pancreatic, ovarian, prostate, etc. In some aspects, relevant terms to be extracted by the drug terms extractor may be provided (e.g., by a subject matter expert) wherein the search terms comprise genes, gene synonyms, gene variants, gene variant synonyms, drugs, drug synonyms, diseases, disease synonyms or cancer-types and cancer-type name synonyms.

Extracted omics data 41 may include information regarding genes/gene variants associated with diseases, RNA translation levels associated with diseases, protein expression levels associated with diseases, etc. for a population of patients. In some cases, the data may be grouped to form a cohort based upon common features of the population of patients.

Patient-specific data 43 may include omic data specific to the patient (not data from a population of patients) along with other medical history data (e.g., drug allergies, age, medical conditions, other medications to assess for contraindications, etc.) for the specific patient.

Drug ranking data 44 may include rankings of a list of drugs for a specific disease, such as a type of cancer. In some cases, the rankings may reflect a population of patients, rather than specific information for a particular patient. In other cases, the rankings may be refined to be specific to a particular patient, considering patient-specific oncogenic mutations, drug allergies, contraindications from other medications, etc. that may apply to that patient.

Drug ranking system 15 may include one or more modules or units to perform the various functions of present invention embodiments described herein. The various modules (e.g., drug terms extractor 71, omics extractor 72, machine learning module 73, biological pathways module 74, drug ranking module 75, etc.) may be implemented by any combination of any quantity of software and/or hardware modules or units, and may reside within memory 17, 23 of the server and/or client systems for execution by processor 16, 22.

Drug terms extractor 71 parses literature in machine readable form (e.g., such as scientific or clinical publications comprising information including clinical information, etc. and/or databases to identify information relating to a specific drug for a particular therapeutic target of a biological pathway). In some cases, the drug terms extractor 71 may comprise natural language processing (NLP) module 76, which may be configured to identify gene/gene variant names, protein names, drug names, biological targets, characteristics of drugs (e.g., efficacies, potencies, toxicities, secondary effects, IC50, ED50, etc.) and synonyms thereof. NLP-based tools may semi-autonomously extract evidence related to drug characteristics based on gene alteration, gene variant alteration, and gene pathway alteration. These drugs may be ranked in terms of their characteristics at the gene level, gene variant level, and/or biological pathway level.

In some aspects, drug terms extractor 71 relies on data from pre-clinical, clinical, and post-clinical studies (instead of just in vitro studies), limiting drugs to those that are approved by a regulatory agency or otherwise available from a clinical trial. Often, the mechanism of the drug is known.

Additionally, gene name synonyms, gene variant name synonyms, drug name synonyms and cancer-type name synonyms may be identified by drug terms extractor 71 and linked to the common name, in order to be included in this analysis.

In some cases, the system may be provided with a list of drug names (and synonyms) that are approved by the FDA or in clinical trials. For example, the system may be provided with the tradename, generic name, structural name, and/or reference ID (e.g., from a database of drugs) pertaining to the drug, etc. in order to identify and extract relevant information from the literature. In some aspects, drug terms extractor 71 may extract any suitable information to determine characteristics of a cancer drug including but not limited to efficacy, toxicity, potency, etc., terms pertaining to success of the clinical trial, terms pertaining to failure of the clinical trial, number of clinical trials, phase of clinical trial, drug side effects, drug interactions, drug structures, etc. In some cases, terms pertaining to the biological target (e.g., protein, cell surface target, cell target, intracellular target, extracellular target, etc.) may also be extracted by the drug terms extractor 71, while in other cases, information pertaining to the biological target may be provided by subject matter experts.

Clinical documents (e.g., including pre-clinical, clinical and post-clinical documents and databases) may be identified and the extraction of relevant information automated. In some cases, the extracted information may be curated by subject matter experts (e.g., for particular types of cancer). Any suitable source may be used including experimental/research articles, drug discovery articles, pre-clinical articles, clinical articles, post-clinical articles, etc.

For each drug, a variety of different types of drug related information may be extracted, including but not limited to drug name (including generic names and synonyms), gene/protein or other biological targets of drug (primary target), toxicity of drug, off-target effects (secondary targets that the drug binds to), structure of drug, potency, ED50, IC50, adverse events, patient specific information, drug efficacy, etc. Off target effects may refer to a drug that binds to a secondary target with lower affinity as compared to the primary target and may cause a biological effect that may adversely impact a toxicity profile of the drug.

In some cases, the extracted information may be organized according to cancer type for analysis, according to age ranges, according to gender, according to biological pathway, according to gene/gene variant, or any other category suitable for generating a cohort of data as compared to the specific patient. Extracted information may be stored as structured text or unstructured text or as a combination thereof.

Omics extractor 72 may access omic data from various databases (e.g., public, private, etc.), which contain data from genomics, epigenomics, transcriptomics, proteomics, metabolomics, etc. studies. The omics extractor 72 may contain one or more extractors tailored to extract each type of biological data. For example, a genomic/epigenomic extractor may extract and analyze genomic/epigenomic data including genes, gene variants, as well as genetic alterations and mutations associated with cancer. A transcriptomic extractor may extract and analyze RNA expression profiles in cancerous biological samples (e.g., to analyze RNA profiles showing overexpression, underexpression, or similar expression to noncancerous controls). A proteomic extractor may extract and analyze protein expression profiles in cancerous biological samples (e.g., proteins that are overexpressed, under expressed or are about the same as compared to noncancerous controls). Similarly, a metabolomic extractor may extract and analyze metabolic data in cancerous biological samples. Biological data may include any suitable format, including sequencing data, hybridization microarrays, transcription microarrays, expression microarrays, metabolic microarrays, etc.

Machine learning module 73 may be trained on extracted data to identify new relationships between drugs and biological targets, to identify causes of toxicity, such as off target effects including interactions with a gene/gene variant protein/protein variant linked to a toxicity effect, etc. Machine learning module 73 may be provided with training data comprising information about known drugs, including structure, toxicity, biological targets, potency, efficacy, and off target effects, etc. Machine learning module may predict any of these features (e.g., toxicity, biological targets, potency, efficacy, and off targets, etc.) for drugs to be analyzed.

Machine learning module 73 may use any suitable machine learning technique, including but not limited to statistical classification, supervised learning, unsupervised learning, artificial neural networks, deep learning neural networks, cluster analysis, random forest, dimensionality reduction, binary classification, decision tree, etc. to predict various features, including but not limited to toxicity, biological targets, potency, efficacy, and off targets for drugs.

Biological pathways module 74 maps information from drug terms extractor 71 and/or omics extractor 72 to biological pathways. For example, a drug may be known to interact with a first target (primary target), wherein the target may be a gene, gene variant, transcript, protein, metabolite, etc. associated with an omic data set. The biological pathway module 74 may map the first target to a first biological pathway.

In some cases, biological pathways module 74 may map secondary effects (off target) to biological pathways. This may be repeated for multiple drugs, allowing secondary effects from multiple drugs to be mapped to one or more biological pathways. Biological pathways may be determined based on predetermined groups of genes. In some cases, biological pathways may be associated with toxicity. Drugs that interact with these pathways, through primary or secondary effects may be ranked lower than drugs that do not interact with these pathways. Thus, not only may biological pathways determine a drug that is suitable for a specific mutation in a patient, but the biological pathways may also be used to prioritize drugs that do not interact with toxicity associated pathways.

Drug ranking module 75 may accept inputs from the biological pathways module 74, the drug terms extractor 71, machine learning module 73, and/or the omics extractor 72 as well as patient specific data 43. A set of drugs suitable for the specific patient may be provided to the drug ranking module 75, and the module may rank the drug based on positive factors of effectiveness that result in a higher ranking (e.g., good efficacy, high potency (e.g., nM or pM range), no known secondary targets, low toxicity, etc.), or negative factors of effectiveness that result in a lower ranking (e.g., limited efficacy, low potency, multiple secondary targets, high toxicity, etc.). Drugs targeting relevant biological pathways may be identified based upon patient-specific data, and the extracted information regarding characteristics of drugs may be used to rank drugs for a specific patient based on omics and other data (e.g., tumor type, tumor mutation, clinical data, medical history, etc.). Based on the received information, the drug ranking module ranks the set of drugs for a specific patient, which may be stored in drug ranking data 44.

Present techniques offer high granularity regrading drug interactions, efficacies, and other characteristics and may be tailored to identify optimal treatments for specific patients.

Figure 2:
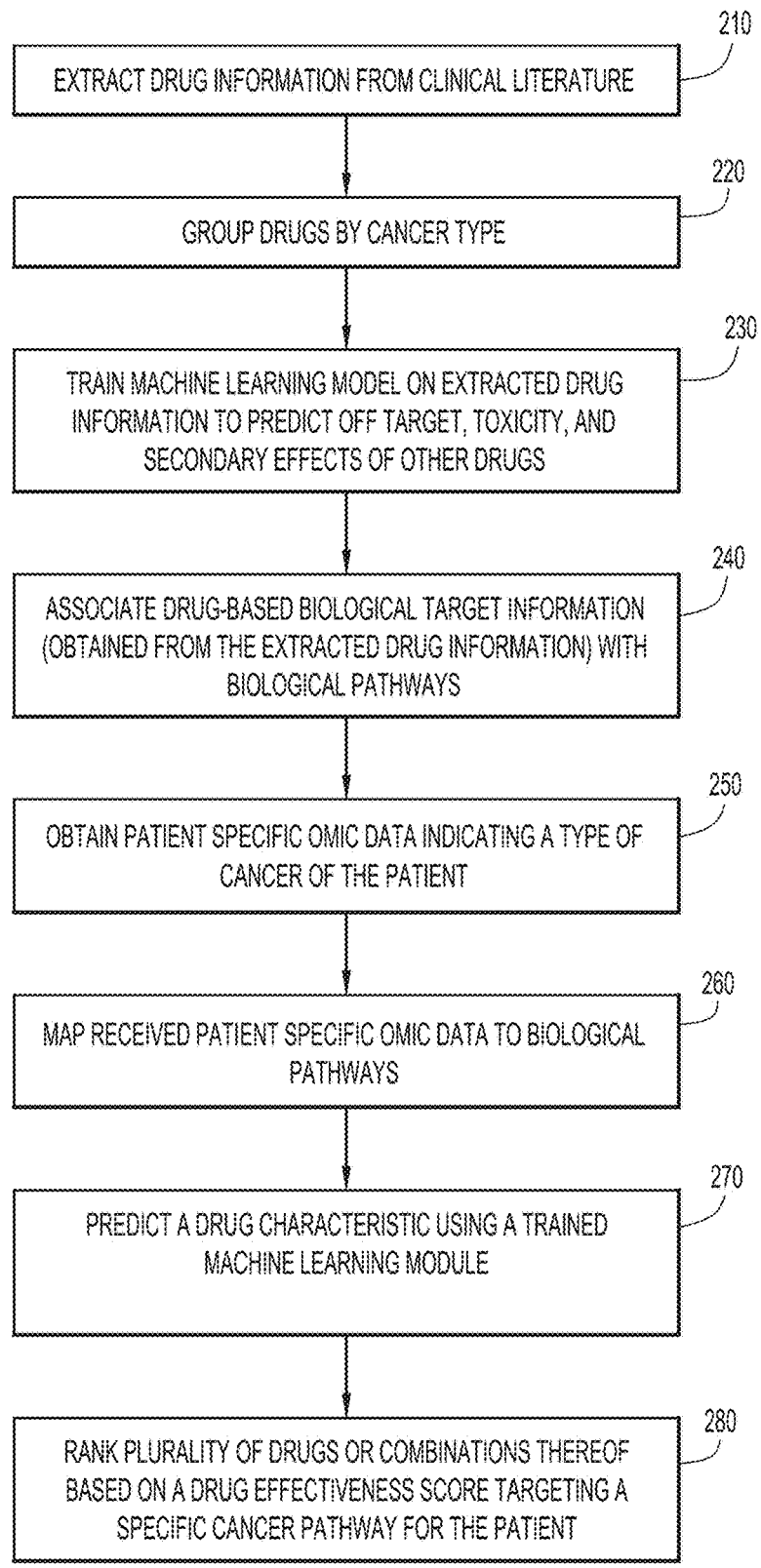
FIG. 2 is an example flow chart of a manner of ranking drugs based on a drug effectiveness score, according to embodiments of the present disclosure.

FIG. 2 is a flow chart of example operations for determining drug rankings. At operation 210, drug information is extracted from clinical literature. Drug information may include but is not limited to primary targets, efficacy, toxicity, side effects, potency, ED50, IC50, etc. At operation 220, drugs are optionally grouped by cancer type, gene mutation and/or possibly other patient-specific factors. At operation 230, a machine learning model is trained on the extracted drug information to predict potency, efficacy, primary effects, biological targets, toxicity, secondary effects (off target effects), etc. for other drugs lacking characteristics extracted from the literature. In some cases, the machine learning module may predict if the cancer drug is associated with a risk of the patient developing a secondary disease or cancer over time. At operation 240, drug-based biological target information (obtained from the extracted drug information) is mapped to biological pathways.

At operation 250, patient specific omic data is obtained, e.g., indicating a type of cancer of the patient and one or more types of omics information, which may include genomic sequences (e.g., including mutations that are associated with cancer, presence of specific driver genes that are associated with cancer, genes, gene variants, etc.), RNA expression levels (e.g., including specific transcripts associated with cancer), protein expressions levels (e.g., including one or more biomarkers associated with cancer, overexpression and/or underexpression, etc.). In some aspects, omics data may be analyzed and provided by the omics service provider (e.g., a company performing genomic sequencing and/or offering microarray analysis or other services to evaluate gene translation, protein expression, etc.) A report may be provided to the patient or medical provider regarding the results of the report, and may identify a genomic mutation, a gene variant, or specific proteins/transcripts associated with cancer.

At operation 260, patient specific omics data is mapped to biological pathways. For example, if the patient specific data shows a mutation in a particular protein or gene of a biological pathway, the system will identify the protein's or gene's presence in a biological pathway. Once the targets are known, the drug ranking system may determine which drugs are most suitable for administration. In some cases, drugs may be mapped to the biological pathway (e.g., to determine which drugs act on a biological pathway containing the patient-specific mutation). Secondary effects may also be mapped to the biological pathway. In some cases, secondary effects (off target binding) may be associated with toxicity or other undesirable drug characteristics. Biological pathways may be identified that are associated with toxicity, and used to identify other drugs that may have toxicity issues, based on interaction with these identified pathways. At operation 270, a machine learning module is trained on the extracted information, and used to predict drug characteristics. At operation 280, a plurality of drugs (or combinations thereof) are ranked based on a drug effectiveness score to target specific cancer pathways relevant to the patient's omics information and cancer type. The drug effectiveness score may reflect weighted combinations of various drug characteristics (e.g., efficacy, toxicity, potency, etc.).

Figure 3:
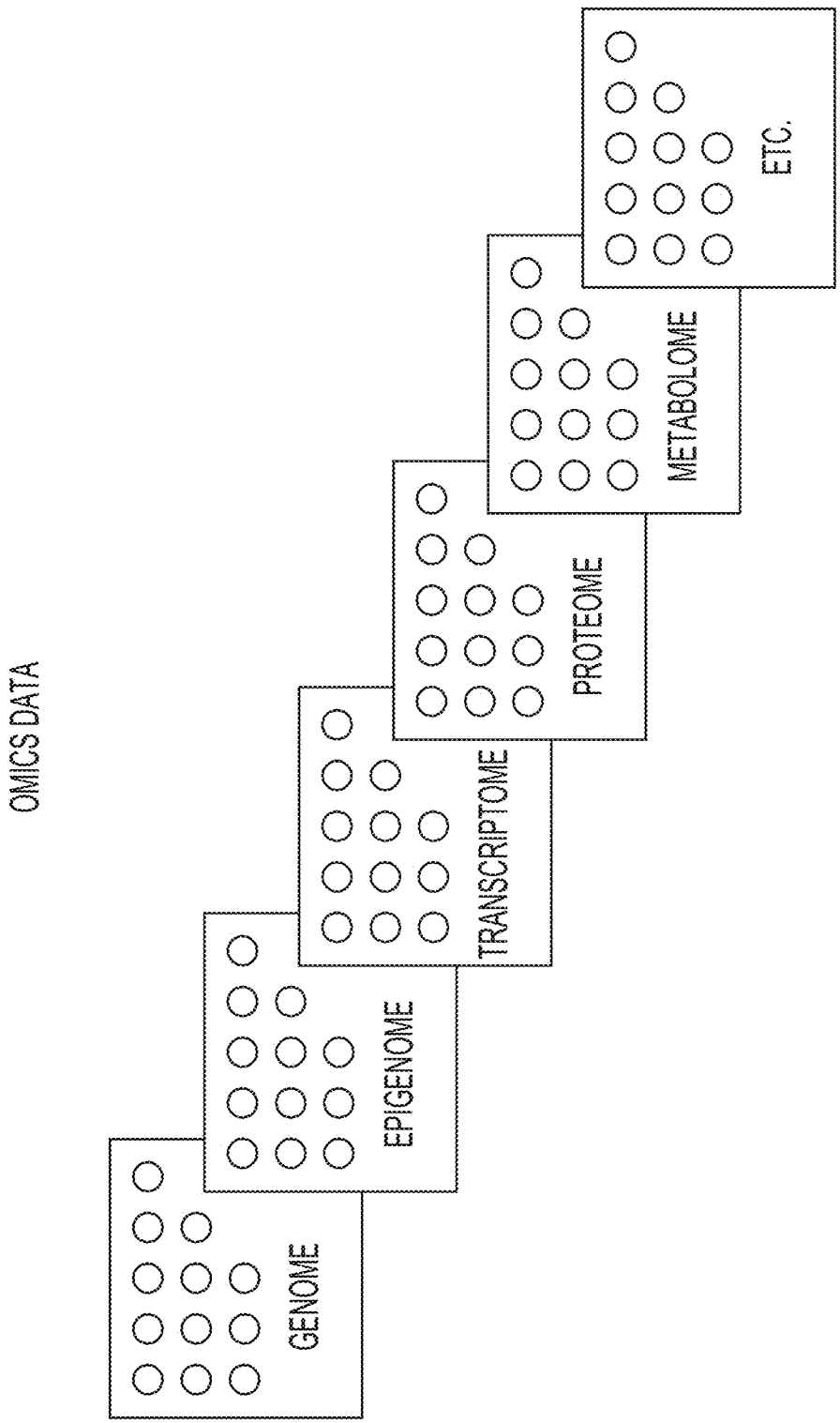
FIG. 3 is an illustration showing an example of different types of omic data, according to embodiments of the present disclosure.

FIG. 3 shows omics data that may include but is not limited to data from genomics, epigenomics, transcriptomics, proteomics, metabolomics, etc. studies. In some aspects, omics data may be obtained from publicly available databases, which may include publications, sequences, expression or transcription levels from microarray analyses, other results of omics studies, etc. Omics data may include data from a population of patients and may be extracted and stored in extracted omics data 41.

For each of these categories, the data may be analyzed to identify various cancer related targets. For example, genomic/epigenomic data may be analyzed to identify genes and mutations associated with cancer, as well as transcription and expression levels of molecules involved in the development and pathogenesis of cancer. Certain types of cancer may have specific transcription or expression profiles, which are associated with a biological pathway. This information may be mapped to biological pathways to indicate oncogenic mutations and other oncogenic factors.

Thus, omics extractor 72 may identify specific information (e.g., mutations, transcription profiles, expression profiles, etc.) that are associated with specific types of cancer for a population of individuals. This information may be stored as extracted omics data 41.

When patient specific information (e.g., patient specific data 43) is provided to the system, biological pathways with cancer related information from mapped population based omics information may be used to identify potential drug targets for specific biological targets and/or pathways associated with the specific patient. Patient specific data 43 may include genomic information, transcriptomic information, proteomic information, metabolic information, etc. or any other suitable pharmacological or experimental information pertaining to the specific patient. Based on this approach, specific biological targets and/or pathways may be identified as potential drug targets for the patient.

Figure 4:
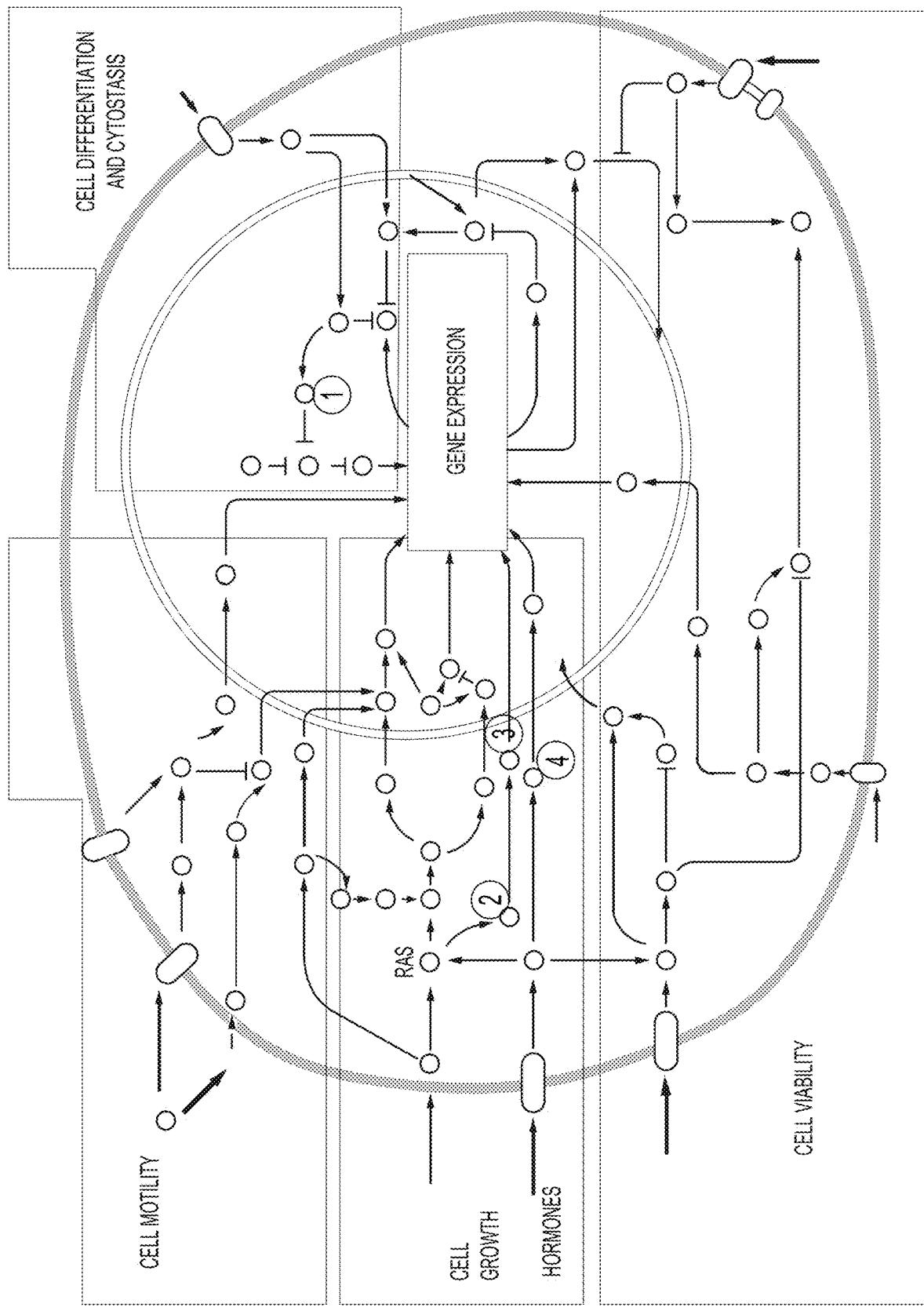
FIG. 4 is an illustration showing an example of different biological pathways specific to cancer, according to embodiments of the present disclosure.

FIG. 4 shows various biological pathways. In this example, the pathways are shown arranged according to categories including cell motility, cell growth, cell viability, and cell differentiation and cytostasis. The nodes represent various entities (e.g., proteins, chemical molecules, etc.) in the pathway which have a particular biological/chemical structure. The black arrows show interconnectivity between nodes of biological pathways. In this example, the outer circle represents an outline of the cell, whereas the inner circle represents an outline of the nucleus.

A variety of biological pathways may be targeted in a variety of manners including extracellularly, at the cell membrane, inside the cell at the cytoplasmic level, as well as inside the nucleus which controls gene expression.

Example biological targets are shown as open circles, which correspond to various potential biological targets of drugs. Target 1 (circle containing number 1) corresponds to a drug target (e.g., for a particular drug) with no known secondary interactions. Target 2 (circle containing number 2) corresponds to another drug target. Targets 3 and 4 represent secondary targets of still other drugs associated with toxicity.

In the cell growth category, targets 3, 4 are present along the same biological pathway, both of which reflect secondary targets, and are associated with drug toxicity. In this case, the drug ranking module would consider any target 2 along this same biological pathway to be associated with toxicity and therefore may not prioritize drugs along this pathway over drugs in other non-toxic pathways.

Additionally, drugs that target the same gene, same gene variant, or same biological pathway may be grouped and the corresponding efficacy, toxicity, side effects, potency, ED50, and IC50 for each drug with respect to a category may be determined. In some cases, a single oncogene may be targeted by different drugs having different characteristics. The drug ranking system may rank the drugs in a patient-specific manner, based on the specific drug and/or the patient-specific omics profile.

FIG. 5 shows an example of analyzing a plurality of drugs and discovering new patterns and relationships between drugs and their targets. For example, a first drug (drug 1 profile) and a second drug (drug 2 profile) may bind to the same biological target (gene X or protein Z). The toxicity of the first drug is not known, but may be derived based on extracted information using a machine learning module.

A machine learning module may be used to determine drug characteristics. Training data may be provided to the machine learning module as drug profiles. Once trained, the machine learning system may predict whether drug 1 with an unknown toxicity may have a toxic side effect. In this case, the machine learning system may be trained on a plurality of drug profiles which link toxicity to secondary biological targets. From this information, the machine learning module may determine that drug 1, which binds to secondary biological targets is also likely to have toxic side effects. Accordingly, in this example, drug 2 may be selected for patient administration to treat a particular type of cancer, as the first drug is associated with secondary biological targets linked to toxicity, an undesirable side effect.

As another example, the profiles of a plurality of drugs may be evaluated for toxicity. Drugs having a toxicity above a threshold may be grouped together, and the drugs may be evaluated for common features that are linked to the toxicity. For example, if a group of drugs interact (secondary effect) with a gene or protein associated with toxicity, the group of drugs may be evaluated for common structural features (e.g., presence of a particular side chain, heterocyclic group, etc.) that may be common to all the drugs, and therefore, likely associated with the toxicity. In FIG. 5, drug 3 may be flagged as potentially having toxicity due to the presence of side chain A1, a feature common to a plurality of other drugs known to have toxicity. Additionally, new drugs having these same features may be flagged for toxicity. A drug not associated with toxicity may be selected for administration to the patient.

As yet another example, a group of genes may be evaluated for synergy or lack of synergy. A drug interacting with a first group of genes via off target effects (e.g., interacts with A, R, Y genes→demonstrates synergy and does not have toxicity) would be selected over another drug interacting with a second group of genes (e.g., interacts with A, D, Y genes→demonstrates lack of synergy and has toxicity).

As yet another example, patients that respond to a drug with a particular side effect may be evaluated to identify causes of the side effect. For example, if about three percent of a patient population exhibits a toxicity effect when taking a specific drug, the patient-specific data from the adverse population can be compared to a control population (those taking the drug without the side effect), to determine features potentially responsible for the off target effect (e.g., genetic commonalities in the adverse population, commonalities in medical history, etc.). For example, three percent of patients may have a mutation in a gene, which may lead to an adverse effect, e.g., from the drug binding to (increased affinity) the corresponding mutated protein.

Accordingly, these techniques allow profiles to be generated for individual drugs, based on extracted information and machine learning, and the drugs may be scored and ranked using the ranking module 75 to determine effective drugs for a given patient with a particular type of cancer.

Figure 6:
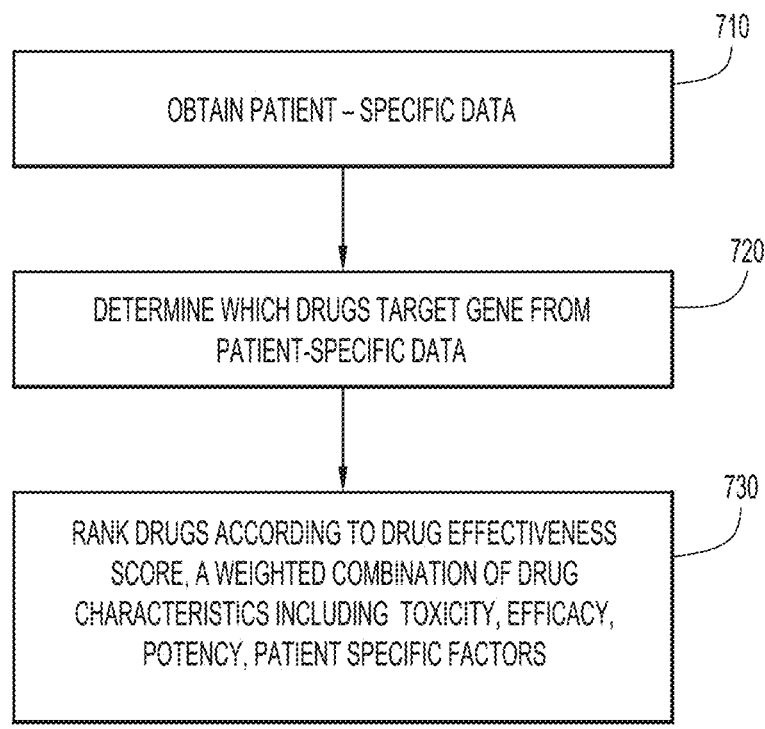
FIG. 6 is an illustration showing an example flowchart of ranking drugs based on drug characteristics, according to embodiments of the present disclosure.

FIG. 6 shows a flow chart for ranking drugs. Initially, rankings may be limited to strong, intermediate, and low categories. Once the machine learning module is trained, drugs may be ranked numerically, wherein the rank is based on any one or more of a toxicity, a potency, ED50, IC50, a clinical efficacy, etc. for a given biological target. For the ranking, extracted data (e.g., genes, gene variants, biological targets, etc.) may be mapped to biological pathways, which may also be extracted from the literature.

At operation 710, patient specific data is obtained, and may be used to determine a biological target to treat the patient's cancer. At operation 720, the system 15 determines which drugs target the gene/gene variant/biological pathway identified from the patient-specific data. At operation 730, differentially weighted concepts relating to drug effectiveness are applied to each drug and a drug effectiveness score may be calculated. The drug effectiveness score may represent different characteristics of the drug, depending on what concepts/weights are applied, including but not limited to efficacy, toxicity, potency, patient-specific factors (e.g., omic information, medical history), etc. Efficacy is the maximum effect of a drug (regardless of dose). Potency is the amount of a drug that is needed to produce a specified effect. Toxicity corresponds to an amount of a drug leading to an adverse effect (e.g., difficulty breathing, organ damage etc.).

In some cases, drugs that target the same gene, gene variant and/or signaling pathway may be grouped together, and each ranked using differentially weighted concepts related to drug effectiveness that are applied to each drug. A drug effectiveness score is calculated, wherein the drug effectiveness score may represent different characteristics of the drug, depending on what concepts/weights are applied.

In other cases, each drug may be ranked based on a drug effectiveness score in terms of effectiveness (e.g., using differentially weighted concepts related to drug characteristics including toxicity, efficacy, secondary effects, potency, etc.) at the gene, gene variant and/or signaling pathway level (not limited by the same target).

In some aspects, drug ranking may assign drugs to tiers, with tier 1 having highest/best efficacy based on the tumor response or IC50 value; tier 2 having moderate/mid efficacy based on the tumor response or IC50 value; and tier 3 having low/no efficacy based on the tumor response or IC50 value. In some cases, drugs that target the same gene, same gene variant, same biological pathway may be grouped by tier level.

Thus, drugs may be ranked according to tiers (without being limited to the same gene, variant, or pathway). Once tier ranking is complete, each tier may undergo further ranking, by grouping drugs that target the same gene/gene variant or biological pathway.

Additional types of information may be provided about specific drugs, such as regulatory approval status (in the FDA and in non-US countries), known associations with drug resistance, whether the drug passes the blood-brain barrier, and the chemical structure of the drug, which may be considered in the analysis and ranking as well.

This information may be integrated into a data management portal for case management. Drugs that target a specific gene, gene mutation, or biological pathway may be presented to a physician or other health care provider with drug rankings to drive selection of treatment options for a patient with a particular gene alteration, gene mutation or biological pathway alteration.

Figure 7:
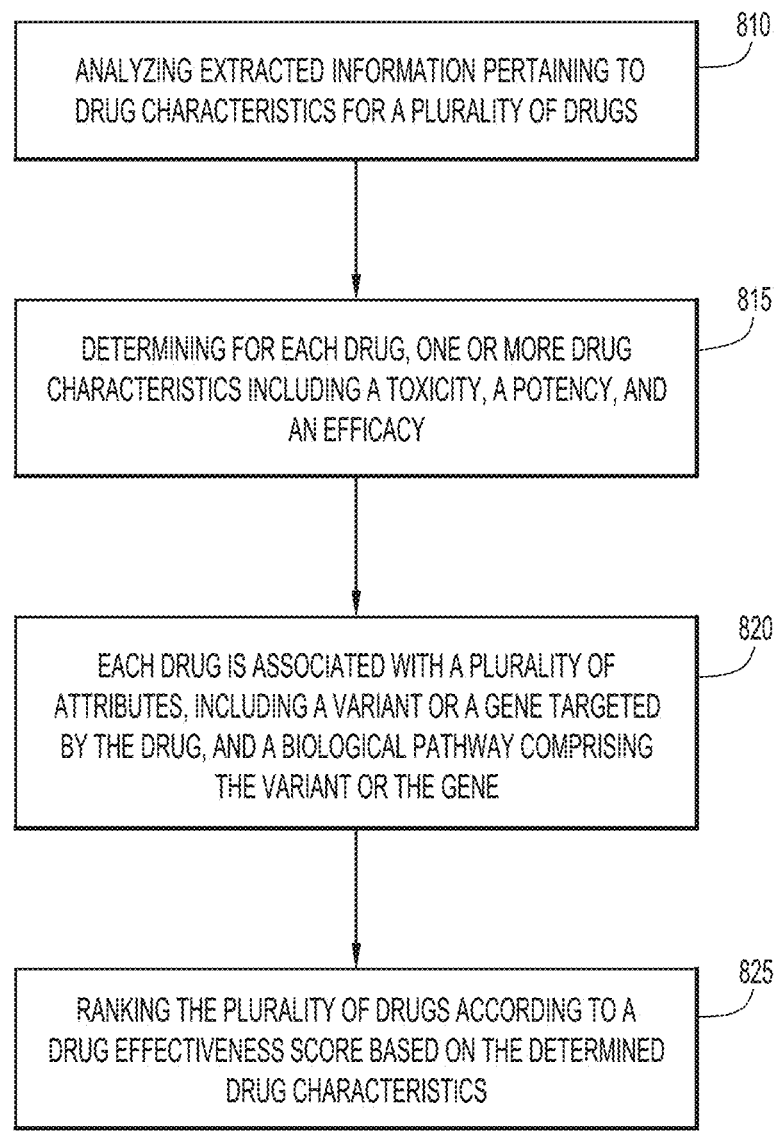
FIG. 7 is a high level flow diagram showing a manner of ranking drugs, according to embodiments of the present disclosure.

FIG. 7 shows a flow chart of example operations. At operation 810, extracted information pertaining to drug characteristics for a plurality of drugs is analyzed. At operation 815, for each drug, one or more drug characteristics are determined. Drug characteristics may include a toxicity, a potency and an efficacy. At operation 820, each drug is associated with a plurality of attributes, including a variant or a gene targeted by the drug, and a biological pathway comprising the variant or the gene. In some cases, gene names may include gene name synonyms and gene variant name synonyms, and drug names may include drug name synonyms. At operation 825, the plurality of drugs are ranked using a drug effectiveness score based upon one or more drug characteristics selected from the group consisting of efficacy, potency, and/or toxicity.

Drugs may be combined based on one or more of the following criteria including specific diseases, genes, gene synonyms, gene variants, gene variant synonyms drugs, drug name synonyms, cancer-types and cancer-type name synonyms.

Present techniques provide a variety of advantages over existing approaches including generating a multi-tiered system to rank drugs impacting the same target. The first tier may include extracting genes, gene variants, and/or signaling pathways from literature and/or databases. The second tier ranks each drug in terms of efficacy or other drug characteristics (e.g., toxicity, secondary effects, potency, etc.) at the gene, gene variant and/or signaling pathway level. The third tier group ranks drugs together that target the same gene, gene variant and/or signaling pathway. Present techniques may use also preclinical data (extracted IC50 values) and/or clinical trials (potency) from the literature for ranking drugs. Cancer-specific information may be extracted, and utilized in conjunction with machine learning for personalized genomics-based medicine.

It will be appreciated that the embodiments described above and illustrated in the drawings represent only a few of the many ways of implementing embodiments for ranking drugs according to administration (e.g., efficacy, toxicity, patient specificity, potency, off target effects, etc.).

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, drug ranking system, etc.). These systems may include any types of monitors and input devices (e.g., keyboard, mouse, voice recognition, etc.) to enter and/or view information.

It is to be understood that the software (e.g., drug terms extractor 71, omics extractor 72, machine learning module 73, biological pathways module 74, drug ranking module 75, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., drug terms extractor 71, omics extractor 72, machine learning module 73, biological pathways module 74, drug ranking module 75, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., extracted omics data 41, extracted literature data 42, patient specific data 43, drug ranking data 44, etc.). The database system may be implemented by any number of any conventional or other databases, data stores or storage structures (e.g., files, databases, data structures, data or other repositories, etc.) to store information (e.g., extracted omics data 41, extracted literature data 42, patient specific data 43, drug ranking data 44, etc.). The database system may be included within or coupled to the server and/or client systems. The database systems and/or storage structures may be remote from or local to the computer or other processing systems, and may store any desired data (e.g., extracted omics data 41, extracted literature data 42, patient specific data 43, drug ranking data 44, etc.).

The present invention embodiments may employ any number of any type of user interface (e.g., Graphical User Interface (GUI), command-line, prompt, etc.) for obtaining or providing information (e.g., extracted omics data 41, extracted literature data 42, patient specific data 43, drug ranking data 44, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include a listing of ranked drugs along with any other information arranged in any fashion, and may be configurable based on rules or other criteria to provide desired information to a user (e.g., efficacies, toxicity, patient-specific, etc.).

The present invention embodiments are not limited to the specific tasks or algorithms described above, but may be utilized for any application in which a ranking of drugs is needed based upon characteristics dispersed throughout a corpus comprising unstructured and/or structured documents.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises a document of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of determining drug characteristics comprising:
analyzing extracted information pertaining to drug administration for a plurality of drugs, wherein the extracted information is extracted using a natural language processing model;
determining for each drug, one or more drug characteristics for a plurality of attributes corresponding to the drug, wherein the attributes include a variant or a gene targeted by the drug, and a biological pathway comprising the variant or the gene;

identifying, for the plurality of drugs, common structural features and corresponding drug characteristics;

identifying which of the drugs are associated with toxicity;

predicting, using a machine learning module trained on information identifying the common structural features and the drug characteristics, other drugs of the plurality of drugs associated with toxicity; and ranking the plurality of drugs according to a drug effectiveness score based on the determined drug characteristics for the plurality of attributes that include the variant or gene targeted by the drug, and the biological pathway comprising the variant or gene, wherein drugs that are more highly associated with toxicity are ranked as less effective according to the drug effectiveness score.

2. The method of claim 1, wherein the drug characteristics are selected from one or more of the group consisting of efficacy, the toxicity, and potency.

3. The method of claim 1, wherein the extracted information comprises pre-clinical, clinical, and post clinical information.

4. The method of claim 3, comprising:

training a predictive machine learning module with the extracted information;

predicting one or more drug characteristics for each drug of the plurality of drugs based on the trained predictive machine learning module; and ranking the drugs for treatment of a patient-specific cancer, wherein each drug targets a particular gene, gene variant, or biological pathway associated with the patient's cancer, and based on the predicted drug characteristics.

5. The method of claim 1, wherein the plurality of drugs are classified into groups based on a common target, and ranking the drugs within each group.

6. The method of claim 1, wherein the attributes comprise patient-specific information indicating the gene, the variant or the biological pathway for a patient, and further comprising:

identifying the plurality of drugs that target the gene, gene variant or biological pathway of the patient; and ranking the identified drugs for the patient based on the drug effectiveness score.

7. The method of claim 1, wherein the extracted information further includes patient-specific omic data.

8. A computer system for determining drug characteristics wherein the system comprises at least one processor configured to:

analyze extracted information pertaining to drug administration for a plurality of drugs, wherein the extracted information is extracted using a natural language processing model;

determine for each drug, one or more drug characteristics for a plurality of attributes corresponding to the drug, wherein the attributes include a variant or a gene targeted by the drug, and a biological pathway comprising the variant or the gene;

identify, for the plurality of drugs, common structural features and corresponding drug characteristics;

identify which of the drugs are associated with toxicity;

predict, using a machine learning module trained on information identifying the common structural features and the drug characteristics, other drugs of the plurality of drugs associated with toxicity; and rank the plurality of drugs according to a drug effectiveness score based on the determined drug characteristics for the plurality of attributes that include the variant or gene targeted by the drug, and the biological pathway comprising the variant or gene, wherein drugs that are more highly associated with toxicity are ranked as less effective according to the drug effectiveness score.

9. The system of claim 8, wherein the drug characteristics are selected from one or more of the group consisting of efficacy, the toxicity, and potency.

10. The system of claim 8, wherein the extracted information comprises pre-clinical, clinical, and post clinical information.

11. The system of claim 10, wherein the processor is further configured to:

train a predictive machine learning module with the extracted information;

predict one or more drug characteristics for each drug of the plurality of drugs based on the trained predictive machine learning module; and rank the drugs for treatment of a patient-specific cancer, wherein each drug targets a particular gene, gene variant, or biological pathway associated with the patient's cancer, and based on the predicted drug characteristics.

12. The system of claim 8, wherein the plurality of drugs are classified into groups based on a common target, and wherein the processor is further configured to rank the drugs within each group.

13. The system of claim 8, wherein the attributes comprise patient-specific information indicating the gene, the variant or the biological pathway for a patient, and wherein the processor is further configured to:

identify the plurality of drugs that target the gene, gene variant or biological pathway of the patient; and rank the identified drugs for the patient based on the drug effectiveness score.

14. The computer system of claim 8, wherein the extracted information further includes patient-specific omic data.

15. A computer program product for determining drug characteristics, the computer program product comprising one or more computer readable storage media collectively having program instructions embodied therewith, the program instructions executable by a computer to cause the computer to:

analyze extracted information pertaining to drug administration for a plurality of drugs, wherein the extracted information is extracted using a natural language processing model;

determine for each drug, one or more drug characteristics for a plurality of attributes corresponding to the drug, wherein the attributes include a variant or a gene targeted by the drug, and a biological pathway comprising the variant or the gene;

identify, for the plurality of drugs, common structural features and corresponding drug characteristics;

identify which of the drugs are associated with toxicity;

predict, using a machine learning module trained on information identifying the common structural features and the drug characteristics, other drugs of the plurality of drugs associated with toxicity; and rank the plurality of drugs according to a drug effectiveness score based on the determined drug characteristics for the plurality of attributes that include the variant or gene targeted by the drug, and the biological pathway comprising the variant or gene, wherein drugs that are more highly associated with toxicity are ranked as less effective according to the drug effectiveness score.

16. The computer program product of claim 15, wherein the drug characteristics are selected from one or more of the group consisting of efficacy, the toxicity, and potency.

17. The computer program product of claim 15, wherein the extracted information comprises pre-clinical, clinical, and post clinical information.

18. The computer program product of claim 15, wherein the program instructions are further executable to:
    train a predictive machine learning module with the extracted information;
    predict one or more drug characteristics for each drug of the plurality of drugs based on the trained predictive machine learning module; and
    rank the drugs for treatment of a patient-specific cancer, wherein each drug targets a particular gene, gene variant, or biological pathway associated with the patient's cancer, and based on the predicted drug characteristics.

19. The computer program product of claim 15, wherein the attributes comprise patient-specific information indicating the gene, the variant or the biological pathway for a patient, and wherein the program instructions are further executable to:
    identify the plurality of drugs that target the gene, gene variant or biological pathway of the patient; and
    rank the identified drugs for the patient based on the drug effectiveness score.

20. The computer program product of claim 15, wherein the extracted information further includes patient-specific omic data.

* * * * *